(12) United States Patent
Ishikawa et al.

(10) Patent No.: US 11,311,242 B2
(45) Date of Patent: Apr. 26, 2022

(54) BIOLOGICAL INFORMATION PROCESSING APPARATUS, BIOLOGICAL INFORMATION PROCESSING METHOD, AND INFORMATION PROCESSING APPARATUS

(71) Applicant: SONY CORPORATION, Tokyo (JP)

(72) Inventors: Takanori Ishikawa, Saitama (JP); Yasuhide Hyodo, Tokyo (JP)

(73) Assignee: SONY CORPORATION, Tokyo (JP)

(*) Notice: Subject to any disclaimer, the term of this patent is extended or adjusted under 35 U.S.C. 154(b) by 531 days.

(21) Appl. No.: 16/300,652

(22) PCT Filed: Mar. 31, 2017

(86) PCT No.: PCT/JP2017/013590
§ 371 (c)(1),
(2) Date: Nov. 12, 2018

(87) PCT Pub. No.: WO2017/199597
PCT Pub. Date: Nov. 23, 2017

(65) Prior Publication Data
US 2020/0305798 A1    Oct. 1, 2020

(30) Foreign Application Priority Data
May 20, 2016 (JP) .............................. JP2016-101094

(51) Int. Cl.
*A61B 5/024* (2006.01)
*A61B 5/0205* (2006.01)
*A61B 5/00* (2006.01)

(52) U.S. Cl.
CPC ............ *A61B 5/721* (2013.01); *A61B 5/0205* (2013.01); *A61B 5/02416* (2013.01);
(Continued)

(58) Field of Classification Search
CPC ............ A61B 5/02416; A61B 5/02422; A61B 5/02427; A61B 5/02433; A61B 5/721;
(Continued)

(56) References Cited

U.S. PATENT DOCUMENTS

| 2003/0212336 | A1* | 11/2003 | Lee ........................ A61B 5/726 |
| | | | 600/504 |
| 2006/0084879 | A1* | 4/2006 | Nazarian ................ A61B 5/721 |
| | | | 600/500 |

(Continued)

FOREIGN PATENT DOCUMENTS

| CN | 104135917 A | 11/2014 |
| CN | 105263403 A | 1/2016 |

(Continued)

OTHER PUBLICATIONS

Elgendi et al., "Systolic Peak Detection in Acceleration Photoplethesmograms Measured from Emergency Responders in Tropical Conditions" PLoS One, 2013 8(10): e76585 (Year: 2013).*

(Continued)

*Primary Examiner* — Colin T. Sakamoto
(74) *Attorney, Agent, or Firm* — Chip Law Group

(57) ABSTRACT

A biological information processing apparatus according to an embodiment of the present technology is provided with a sphygmographic sensor unit, a plurality of calculation units, and an output unit. The sphygmographic sensor unit outputs a pulse wave signal. The plurality of calculation units respectively calculate heart rate candidate information with a reliability on a basis of the output pulse wave signal. The output unit outputs heart rate information on a basis of the heart rate candidate information and the reliability thereof calculated by each of the plurality of calculation units.

12 Claims, 11 Drawing Sheets

(52) U.S. Cl.
CPC .......... *A61B 5/02438* (2013.01); *A61B 5/725* (2013.01); *A61B 5/7214* (2013.01); *A61B 5/7246* (2013.01); *A61B 2562/04* (2013.01)

(58) Field of Classification Search
CPC ............... A61B 5/7214; A61B 5/0205; A61B 5/02438; A61B 5/7246; A61B 5/725; A61B 2561/04
See application file for complete search history.

(56) References Cited

U.S. PATENT DOCUMENTS

| | | | | |
|---|---|---|---|---|
| 2010/0145171 | A1* | 6/2010 | Park | A61B 5/1455 600/324 |
| 2014/0213858 | A1* | 7/2014 | Presura | A61B 5/681 600/301 |
| 2014/0213863 | A1* | 7/2014 | Loseu | A61B 5/7207 600/324 |
| 2015/0046095 | A1 | 2/2015 | Takahashi et al. | |
| 2015/0196257 | A1* | 7/2015 | Yousefi | A61B 5/024 600/324 |
| 2015/0313549 | A1* | 11/2015 | Lee | A61B 5/721 600/479 |
| 2016/0022160 | A1* | 1/2016 | Pi | A61B 5/7225 600/479 |
| 2016/0081630 | A1 | 3/2016 | Aoshima | |
| 2017/0071547 | A1* | 3/2017 | van Dinther | A61B 5/14552 |
| 2017/0086753 | A1* | 3/2017 | Presura | A61B 5/02427 |
| 2017/0164847 | A1* | 6/2017 | Pande | A61B 5/0002 |
| 2017/0209055 | A1* | 7/2017 | Pantelopoulos | A61B 5/7203 |
| 2018/0098701 | A1* | 4/2018 | Blomqvist | A61B 5/02438 |

FOREIGN PATENT DOCUMENTS

| | | | |
|---|---|---|---|
| JP | 11-276448 A | 10/1999 | |
| JP | 2009-039568 A | 2/2009 | |
| JP | 2013-183845 A | 9/2013 | |
| JP | 2014-057622 A | 4/2014 | |
| JP | 2014-236773 A | 12/2014 | |
| WO | WO-9932030 A1 * | 7/1999 | ......... A61B 5/14551 |
| WO | 2014/196119 A1 | 12/2014 | |

OTHER PUBLICATIONS

International Search Report and Written Opinion of PCT Application No. PCT/JP2017/013590, dated Jun. 20, 2017, 10 pages of ISRWO.

* cited by examiner

BIOLOGICAL INFORMATION PROCESSING APPARATUS, BIOLOGICAL INFORMATION PROCESSING METHOD, AND INFORMATION PROCESSING APPARATUS

CROSS REFERENCE TO RELATED APPLICATIONS

This application is a U.S. National Phase of International Patent Application No. PCT/JP2017/013590 filed on Mar. 31, 2017, which claims priority benefit of Japanese Patent Application No. JP 2016-101094 filed in the Japan Patent Office on May 20, 2016. Each of the above-referenced applications is hereby incorporated herein by reference in its entirety.

TECHNICAL FIELD

The present technology relates to a biological information processing apparatus, a biological information processing method, and an information processing apparatus for outputting heart rate information of a user.

BACKGROUND ART

In recent years, in association with a boom of healthcare and wellness, watch type or wristband type devices provided with heart rate sensors for heart rate training have been developed. For those measurement devices, photoplethysmography (hereinafter, referred to as "PPG system") is widely used.

Patent Literature 1 describes a pulsimeter provided with a sphygmographic sensor and a body motion sensor. In the pulsimeter, an adaptive filter is provided in which a pulse wave signal output from the sphygmographic sensor is used as an observation signal, and a body motion signal output from the body motion sensor is used as an input signal. A prediction value of a body motion component calculated by the adaptive filter is subtracted from the pulse wave signal, and a residual signal thereof is subjected to a fast Fourier transformation (FFT) process. From frequency components thereof, a component with a maximum level is extracted as a pulse wave component, and thus a pulse rate per minute is calculated. As a result, an accurate measurement of the pulse rate is performed (Paragraphs [0007] to [0012] of the specification, FIGS. 1A and 1 B, and the like in Patent Literature 1).

CITATION LIST

Patent Literature

Patent Literature 1: Japanese Patent Application Laid-open No. HEI 11-276448

DISCLOSURE OF INVENTION

Technical Problem

As described above, a technology which makes it possible to perform a highly accurate heart rate measurement is being demanded. For example, in a heart rate training or the like, measuring a variation in heart rate in real time with high accuracy is important.

In view of the circumstances as described above, an object of the present technology is to provide a biological information processing apparatus, a biological information processing method, and an information processing apparatus which make it possible to perform highly accurate heart rate measurement.

Solution to Problem

To achieve the object described above, a biological information processing apparatus according to an embodiment of the present technology includes a sphygmographic sensor unit, a plurality of calculation units, and an output unit.

The sphygmographic sensor unit outputs a pulse wave signal.

The plurality of calculation units respectively calculate heart rate candidate information with a reliability on a basis of the output pulse wave signal.

The output unit outputs heart rate information on a basis of the heart rate candidate information and the reliability thereof calculated by each of the plurality of calculation units.

In the biological information processing apparatus, each of the plurality of calculation units calculate the heart rate candidate information with the reliability. Therefore, on a basis the information, it is possible to output the heart rate information with a high reliability. As a result, it is possible to achieve a highly accurate heart rate measurement.

The biological information processing apparatus may further include a body motion sensor that outputs a body motion signal, and a noise reduction processing unit that separates a body motion noise from the pulse wave signal output from the sphygmographic sensor unit on a basis of the body motion signal. In this case, the plurality of calculation units may respectively calculate the heart rate candidate information and the reliability thereof on a basis of the pulse wave signal from which the body motion noise is separated.

On a basis of the pulse wave signal from which the body motion noise is separated, it is possible to calculate the heart rate candidate information with high accuracy. As a result, the highly accurate heart rate measurement is achieved.

The plurality of calculation units may include a first calculation unit that detects a peak position of the pulse wave signal and calculates an instantaneous heart rate on a basis of the pulse wave signal from which the body motion noise is separated.

The instantaneous heart rate can be calculated, so the heart rate variability can be measured with high accuracy.

The first calculation unit may calculate a reliability of the instantaneous the heart rate on a basis of a difference between a local maximum value and a local minimum value of the pulse wave signal.

As a result, it is possible to calculate the reliability with high accuracy.

The plurality of calculation units may include a second calculation unit that detects a period of the pulse wave signal by an autocorrelation analysis and calculates a heart rate on a basis of the pulse wave signal from which the body motion noise is separated.

By the autocorrelation analysis, it is possible to obtain the heart rate on a basis of the heart rate trend.

The second calculation unit may calculate a reliability of the heart rate on a basis of an autocorrelation value in the detected period.

As a result, it is possible to calculate the reliability with high accuracy.

The sphygmographic sensor unit may include a plurality of sphygmographic sensors, and output any one of a plurality of pulse wave candidate signals generated by the plurality of sphygmographic sensors as the pulse wave signal.

As a result, it is possible to perform a highly accurate heart rate measurement.

The noise reduction processing unit may include a first adaptive filter to which the body motion signal that is subjected to a filter process by a transfer function calculated by modeling an influence of a body motion on a bloodstream is input as an input signal, and output a first error signal obtained by subtracting an output value of the first adaptive filter from the pulse wave signal output from the sphygmographic sensor unit.

As a result, it is possible to reduce the body motion noise with high accuracy.

The biological information processing apparatus may further include a generation unit that generates a reference signal for separating the body motion noise on a basis of the plurality of pulse wave candidate signals generated by the plurality of sphygmographic sensors. In this case, the noise reduction processing unit includes a second adaptive filter to which the reference signal is input as an input signal, and outputs a second error signal obtained by subtracting an output value of the second adaptive filter from the first error signal.

The body motion noise is further separated from the first error signal, so it is possible to sufficiently reduce the body motion noise. As a result, the highly accurate heart rate measurement is achieved.

The plurality of sphygmographic sensors may include a first sphygmographic sensor that generates the pulse wave signal, and a second sphygmographic sensor that generates a reference pulse wave signal for generation of the reference signal.

By providing the second sphygmographic sensor that generate the reference pulse wave signal in addition to the first pulse wave signal that generates the pulse wave signal, it is possible to reduce the body motion noise with high accuracy.

The first sphygmographic sensor may include a first light emission unit that emits light in a first wavelength range and a first light reception unit that detects reflection light of the light in the first wavelength range. In this case, the second sphygmographic sensor may include a second light emission unit that emits light in a second wavelength range longer than the first wavelength range and a second light reception unit that detects reflection light of the light in the second wavelength range.

By using the two sphygmographic sensors that emit light having wavelength ranges different from each other, it is possible to perform the highly accurate heart rate measurement.

The biological information processing apparatus may further include a body motion analysis unit that detects a body motion variation by analyzing the body motion signal, and outputs the detected variation as a first body motion analysis result. In this case, the noise reduction processing unit may update an adaptive filter coefficient in the first adaptive filter on a basis of the output first body motion analysis result.

By using the first body motion analysis result, it is possible to reduce body motion noise with high accuracy.

The body motion analysis unit may detect a body motion variation by analyzing the reference pulse wave signal, and outputs the detected variation as a second body motion analysis result. In this case, the noise reduction processing unit may update an adaptive filter coefficient in the second adaptive filter on a basis of the output second body motion analysis result.

By using the second body motion analysis result, it is possible to reduce the body motion noise with high accuracy.

The output unit may output the heart rate candidate information with a highest reliability as the heart rate information.

As a result, the highly accurate heart rate measurement is achieved.

The output unit may determine whether fallback is performed or not on a basis of reliability calculated by each of the plurality of calculation units.

As a result, it is possible to continue the heart rate measurement while preventing the heart rate information with a low reliability from being generated.

The output unit may determine whether the fallback is performed or not on a basis of a reliability calculated with a pulse wave signal from which a body motion noise is separated.

As a result, it is possible to continue the heart rate measurement while preventing the heart rate information with a low reliability from being generated.

A biological information processing method according to another embodiment of the present technology includes generating a pulse wave signal by a sphygmographic sensor.

Heart rate candidate information is calculated with a reliability on a basis of the generated pulse wave signal by each of a plurality of calculation units.

Heart rate information is output on a basis of the heart rate candidate information and the reliability thereof calculated by each of the plurality of calculation units.

An information processing apparatus according to another embodiment of the present technology includes an obtaining unit, a plurality of calculation units, and an output unit.

The obtaining unit obtains a pulse wave signal.

The plurality of calculation units respectively calculate heart rate candidate information with a reliability on a basis of the obtained pulse wave signal.

The output unit outputs heart rate information on a basis of the heart rate candidate information and the reliability thereof calculated by each of the plurality of calculation units.

Advantageous Effects of Invention

As described above, according to the present technology, the highly accurate heart rate measurement can be performed. It should be noted that effects described herein are not necessarily limited, any effect described in the present disclosure may be obtained.

MODE(S) FOR CARRYING OUT THE INVENTION

Hereinafter, embodiments according to the present technology will be described with reference to the drawings.

[Configuration of heart rate measurement apparatus]

Figure 1A:
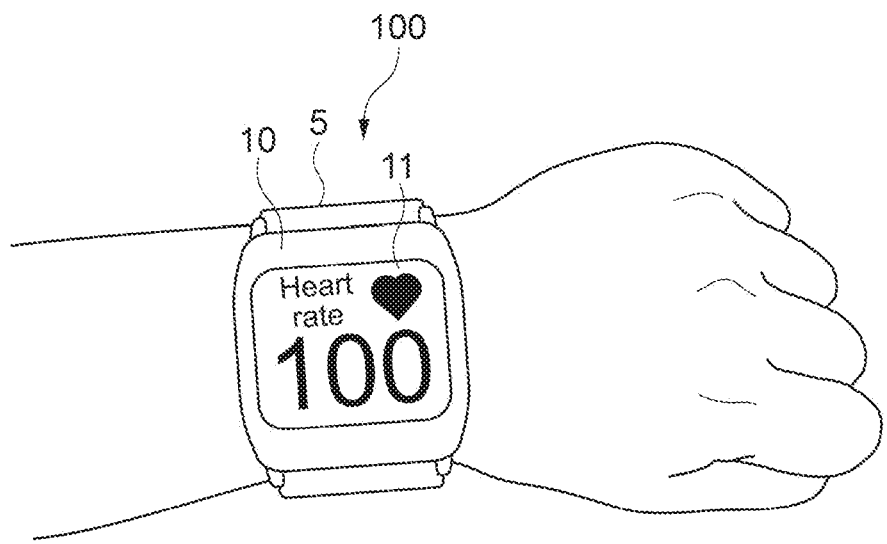
FIGS. 1A and 1B Schematic diagrams showing a configuration example of a heart rate measurement apparatus according to an embodiment of the present technology.
Figure 1B:
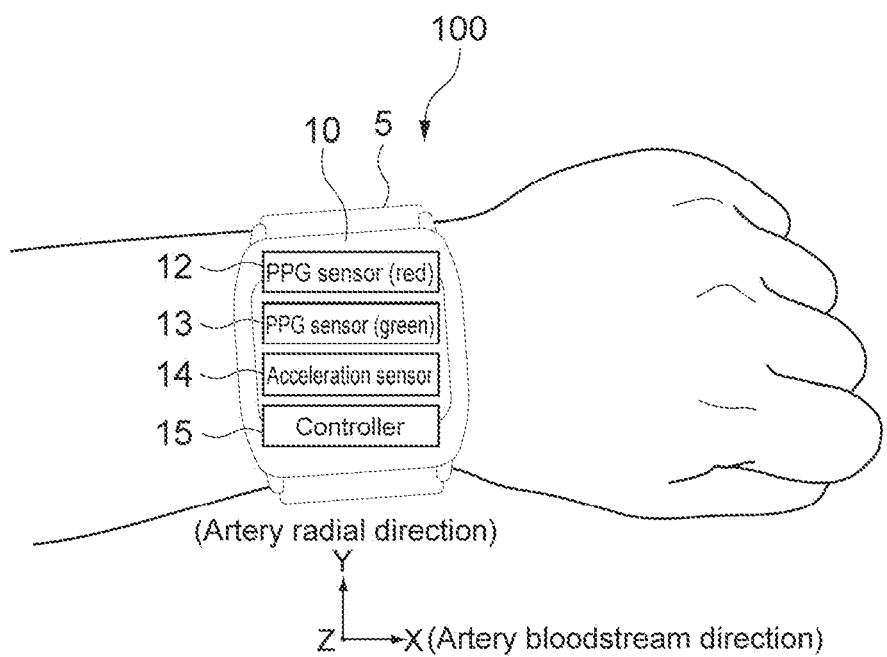

FIGS. 1A and 1B is a are schematic diagrams showing a configuration example of a heart rate measurement apparatus according to an embodiment of the present technology. A heart rate measurement apparatus 100 is a wrist band type heart rate sensor with a PPG system, and is used by being worn around a wrist of a user. In this embodiment, the heart rate measurement apparatus 100 corresponds to a biological information processing apparatus.

The PPG system is a system which measures pulse waves on a basis of a volume variation of bloodstream. In the PPG system, for example, a light emission unit such as an LED (Light Emitting Diode) irradiates a skin with a light beam. The emitted light beam is absorbed in, scattered in, or reflected on blood and subcutaneous tissues which exist under the skin by a depth of approximately several millimeters. At this time, for example, an amount of light which returned from under the skin is measured by a light reception unit such as a photodetector, and thus the bloodstream variation of capillaries distributed under the skin is measured.

As shown in FIGS. 1A and 1 B, the heart rate measurement apparatus 100 includes a wearing band 5 and a sensor main body unit 10. The wearing band 5 is connected with the sensor main body unit 10 and holds the sensor main body unit 10 with the wearing band 5 in contact with a wrist of the user. A specific configuration of the wearing band 5 is not limited.

The sensor main body unit 10 includes a display unit 11 on which a measured heart rate is displayed. The display unit 11 is a display device using liquid crystal, EL (Electro-Luminescence), or the like, for example. As the display unit 11, a touch panel can be configured, and a user operation can be input.

As schematically shown in FIG. 1B, the sensor main body unit 10 includes a first PPG sensor 12, a second PPG sensor 13, an acceleration sensor 14, and a controller 15. The first and second PPG sensors 12 and 13 are provided on a side of a surface in contact with the wrist of the user. Typically, the acceleration sensor 14 and the controller 15 are provided in the sensor main body unit 10.

The first PPG sensor 12 includes a first light emission unit and a first light reception unit (not shown). The first light emission unit emits, as light in a first wavelength range, green light in a green wavelength range (for example, approximately 500 nm to approximately 570 nm) to a measurement portion. The first light reception unit detects an amount of reflection light of the green light returned from under a skin of the measurement portion. The first PPG sensor 12 is provided to measure the bloodstream variation principally.

The second PPG sensor 13 includes a second light emission unit and a second light reception unit (not shown). The second light emission unit emits, as light in a second wavelength range, red light in a red wavelength range (for example, approximately 620 nm to approximately 750 nm) to the measurement portion. The second light reception unit detects an amount of reflection light of the red light returned from under the skin of the measurement portion.

The red light in a long wavelength emitted from the second PPG sensor 13 enters deeply below the skin and reaches tissues of a body. Therefore, for the red light emitted from the second PPG sensor 13, for example, return light is modulated due to deformation of the tissues of the body associated with a motion of a finger and a wrist (motion of a bone). Taking notes of this point, in this embodiment, the second PPG sensor 13 is provided to generate a reference signal having a high correlation with a noise caused by the motion of the finger and the wrist principally.

In this embodiment, the first and second PPG sensors 12 and 13 constitute a sphygmographic sensor unit. The first PPG sensor 12 functions as a first sphygmographic sensor and generates a pulse wave signal. The second PPG sensor 13 functions as a second sphygmographic sensor and generates a reference pulse wave signal to be used to generate the reference signal. Further, the pulse wave signal and the reference pulse wave signal each correspond to a pulse wave candidate signal. Specific configurations of the first and second PPG sensors 12 and 13 are not limited and may be designed as appropriate.

The acceleration sensor 14 measures XYZ triaxial accelerations of the measurement portion on which the heart rate measurement apparatus 100 is put. The acceleration sensor 14 is provided to measure a periodical motion of an arm at a time of walking, jogging, running, or the like principally. The acceleration sensor 14 functions as a body motion sensor, and the triaxial accelerations to be measured are output as body motion signals. A specific configuration of the acceleration sensor 14 is not limited. Further, as the body motion sensor, instead of or in addition to the acceleration sensor 14, a triaxial gyro sensor or the like may be used.

As shown in FIG. 1B, in this embodiment, a right and left direction of the sensor main body unit 10 is set as an X axis direction, and a vertical direction is set as a Y axis direction. Further, a direction orthogonal to the X axis direction and the Y axis direction (perpendicular line direction to a surface of the sensor main body unit 10) is set as a Z axis direction. Further, the X axis direction is regarded as an artery bloodstream direction of the measurement portion, and the Y axis direction is regarded as an artery radial direction. Those are not of course be limited thereto.

The controller 15 controls operations of respective blocks of the heart rate measurement apparatus 100. The controller 15 has a hardware configuration necessary for a computer, such as a CPU and a memory (RAM, ROM), for example. The CPU loads a program stored in the ROM or the like into the RAM and executes the program, and thus various processes are carried out. For example, as the controller 15, a PLD (Programmable Logic Device) such as an FPGA (Field Programmable Gate Array), an ASIC (Application Specific Integrated Circuit), or the like may be used.

In this embodiment, the CPU of the controller 15 executes the program according to this embodiment, with the result that functional blocks to be described below with reference to FIG. 2 or the like are achieved. The functional blocks and the hardware such as the first PPG sensor 12 are cooperated with each other, thereby executing a biological information processing method according to this embodiment. That is, on a basis of the pulse wave signal output from the first PPG sensor 12, heart rate information of the user is generated. To achieve the functional blocks shown in FIG. 2 or the like, hardware dedicated to an IC (integrated circuit) may of course be used.

Figure 2:
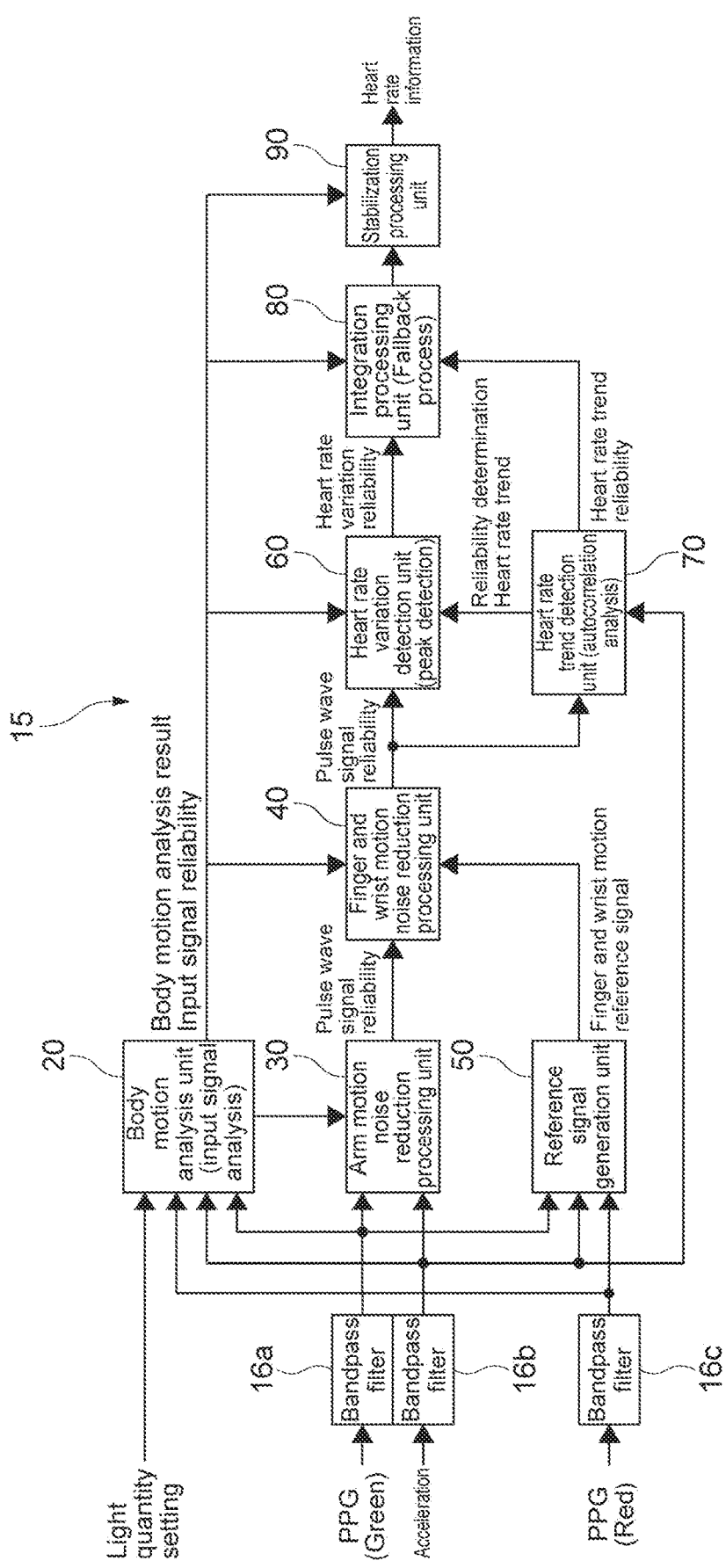
FIG. 2 A block diagram showing a functional configuration example of a controller.

FIG. 2 is a functional block diagram showing a configuration example of the controller 15. "PPG (green)" "acceleration" and "PPG (red)" shown in FIG. 2 are a pulse wave signal from the first PPG sensor 12, a body motion signal from the acceleration sensor 14, and a reference pulse wave signal from the second PPG sensor 13, respectively.

The controller 15 includes bandpass filters 16a to 16c, a body motion analysis unit 20, a first noise reduction processing unit 30, a second noise reduction processing unit 40, a reference signal generation unit 50, a heart rate variation detection unit 60, a heart rate trend detection unit 70, an integration processing unit 80, and a stabilization processing unit 90. As will be described below, when the respective blocks are operated, a heart rate is output as the heart rate information.

[Operation of Heart Rate Measurement Apparatus]

Figure 3:
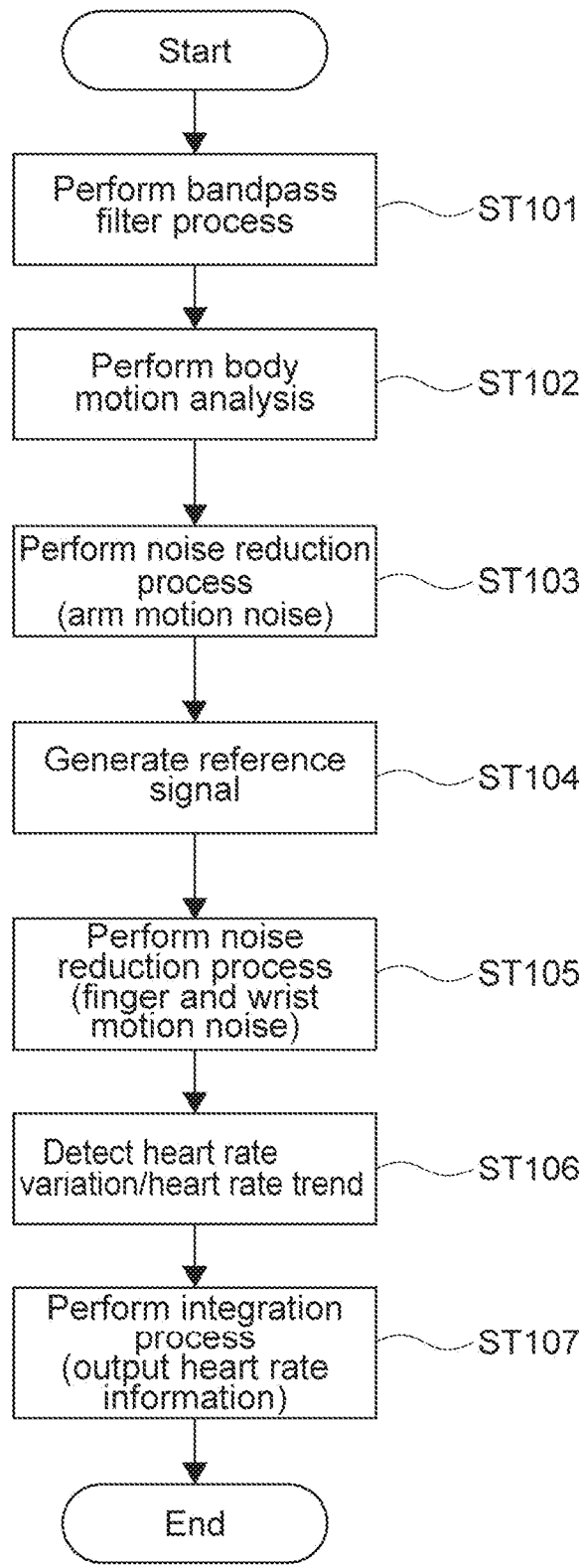
FIG. 3 A flowchart showing an output example of heart rate information.

FIG. 3 is a flowchart showing an output example of the heart rate information. First, the bandpass filters 16a to 16c perform a bandpass filter process (Step 101). The bandpass filters 16a and 16b extract a variation component associated with pulsation or deformation of a body tissue from output signals of the PPG sensors. Further, the bandpass filter 16b performs offset by gravity acceleration and removal of electrical noises.

Figure 4:
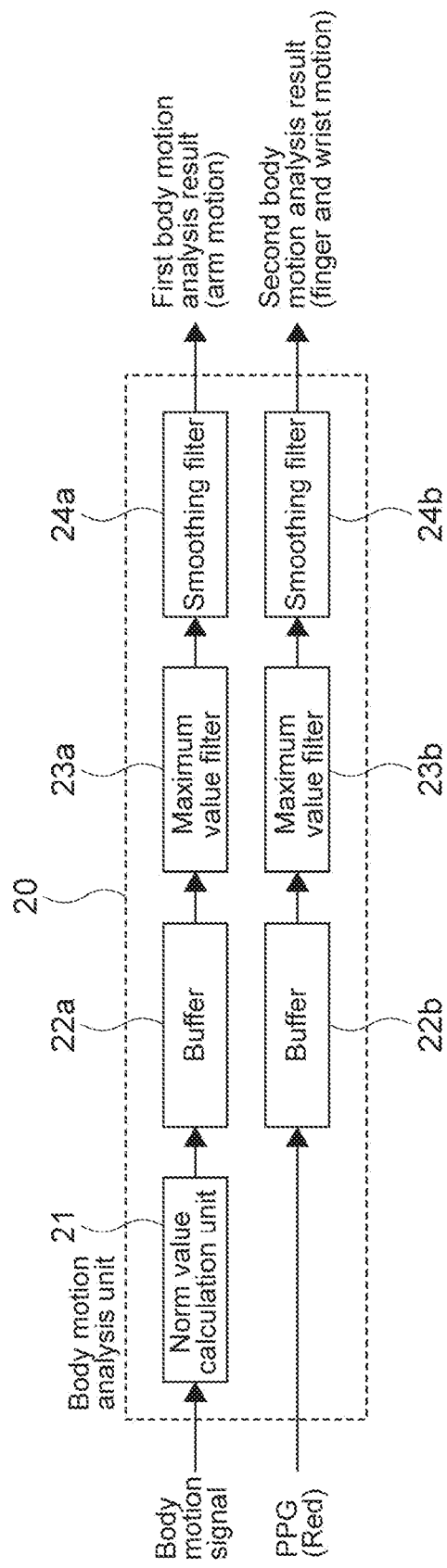
FIG. 4 A diagram for explaining a concept of a body motion analysis by a body motion analysis unit.
Figure 5:
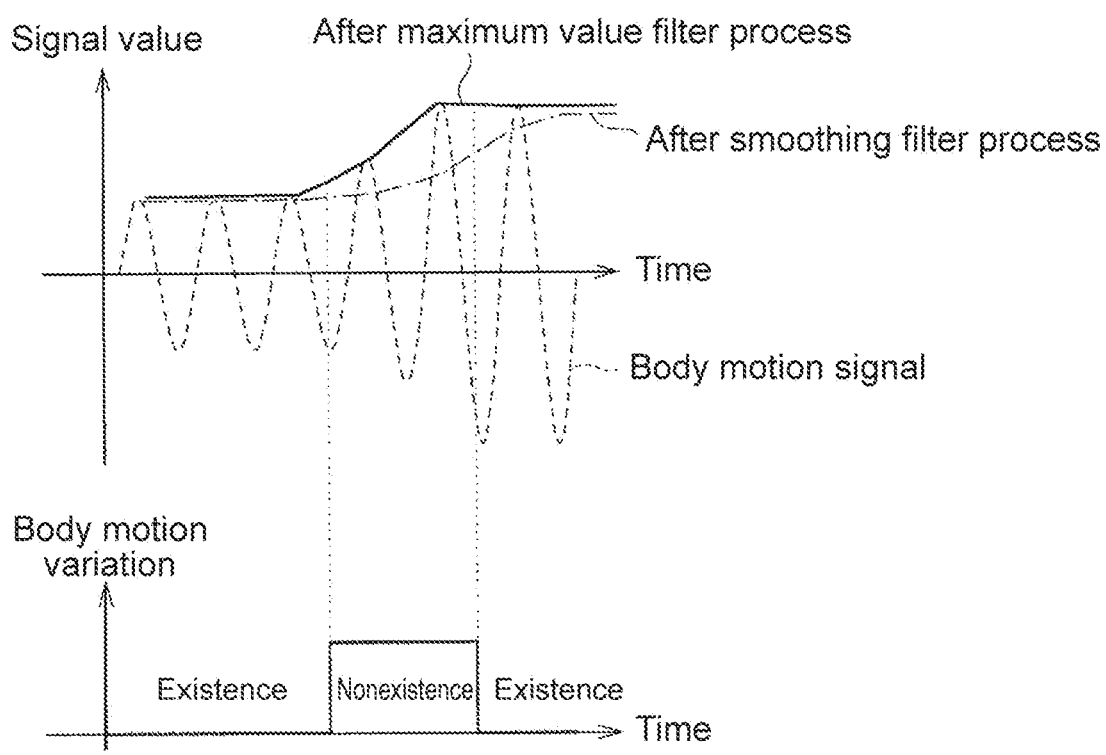
FIG. 5 A diagram for explaining a concept of a body motion analysis by the body motion analysis unit.

The body motion analysis unit 20 analyzes a body motion intensity of the measurement portion (Step 102). FIG. 4 and FIG. 5 are diagrams for explaining a concept of a body motion analysis by the body motion analysis unit 20.

The body motion analysis unit 20 includes a norm value calculation unit 21, buffers 22a and 22b, maximum value filters 23a and 23b, and smoothing filters 24a and 24b. In a case where the acceleration sensor 14 is a triaxial acceleration sensor, the norm value calculation unit 21 calculates an acceleration norm from a triaxial acceleration signal as a body motion signal. The acceleration norm is output to the maximum value filter 23a through the buffer 22a, and a maximum value filter process is performed. The body motion signal (norm value) that has been subjected to the maximum value filter process is output to the smoothing filter 24a, and a smoothing filter process is performed. A threshold value process is performed with respect to a difference between the body motion signal that has been subjected to the maximum value filter process and the body motion signal that has been subjected to the smoothing filter process. As a result, it is possible to detect a variation in body motion at a time when the body motion intensity and body motion frequency of the measurement portion are changed.

In an upper stage in FIG. 5, a vertical axis indicates a signal value, and a lateral axis indicates a time. In a lower stage in FIG. 5, a vertical axis indicates a state of body motion variation (existence or nonexistence of body motion variation), and a lateral axis indicates a time. In the upper state in FIG. 5, the body motion signal before the filter process, the body motion signal after the smoothing filter process, and the body motion signal after the maximum value filter process. For example, from the body motion signal after the smoothing filter process and the body motion signal after the maximum value filter process as shown in the upper state in FIG. 5, it is possible to detect existence or nonexistence of the body motion variation (motion of arm mainly) as shown in the lower state in FIG. 5.

In a similar way, for the reference pulse wave signal output from the second PPG sensor 13, it is possible to detect existence or nonexistence of a body motion variation (motions of fingers and wrist mainly) on the basis of the outputs of the maximum value filter 23b and the smoothing filter 24b. Hereinafter, a term "mainly" may be omitted in some cases.

As described above, the body motion analysis unit 20 outputs a first body motion analysis result for a periodical motion of the arm and a second body motion analysis result for a non-periodical motion of the finger and the wrist. It should be noted that as the smoothing filter, for example, an FIR (Finite Impulse Response) filter, an IIR (Infinite Impulse Response) filter, or the like is used.

Further, as shown in FIG. 2, a set value of a light quantity in each of the first and second PPG sensors 12 and 13 is output to the body motion analysis unit 20. on a basis of the set value, reliabilities of the pulse wave signal and the reference pulse wave signal are calculated. For example, in a case where a light quantity of each light emission unit is lower than a predetermined threshold value, or in a case where the set value of the light quantity is changed, the reliabilities of the pulse wave signal and the reference pulse wave signal are lowered. A method of calculating the reliabilities is not limited, and another method may be used.

The first noise reduction processing unit 30 performs a reduction process for a body motion noise caused due to a motion of an arm (hereinafter, referred to as arm motion noise) (Step 103). It should be noted that in the figure, the first noise reduction processing unit 30 is described as an arm motion noise reduction processing unit 30.

Figure 6:
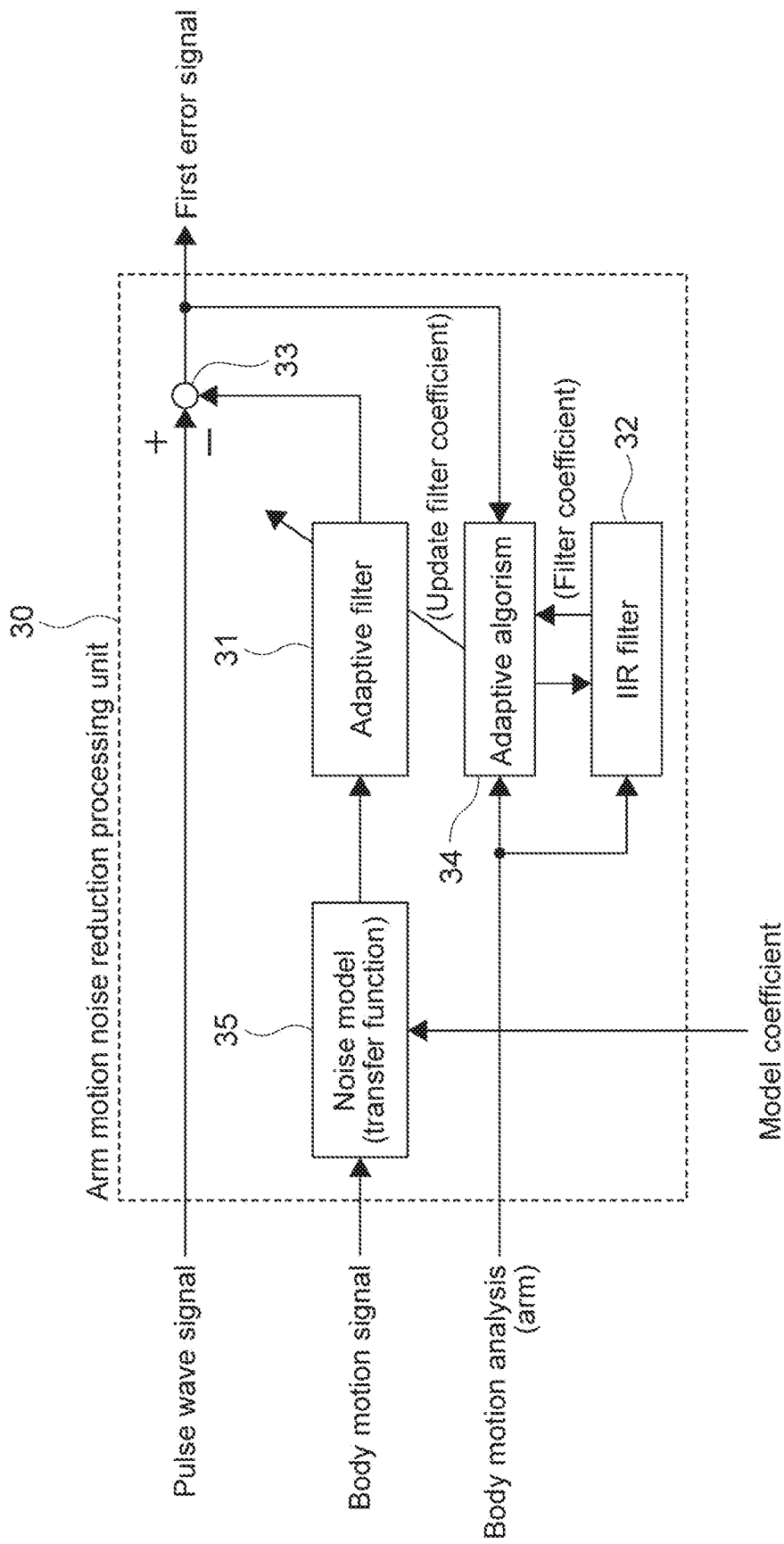
FIG. 6 A block diagram showing a configuration example of a first noise reduction processing unit.

FIG. 6 is a block diagram showing a configuration example of the first noise reduction processing unit 30. The first noise reduction processing unit 30 includes an adaptive filter 31 (first adaptive filter), an IIR filter 32, and a subtractor 33. An input signal of the adaptive filter 31 is a body motion signal, and an observation signal is a pulse wave signal output from the first PPG sensor 12. The subtractor 33 subtracts an output value of the adaptive filter 31 from the pulse wave signal, and outputs a first error signal. The first error signal corresponds to the pulse wave signal from which a body motion noise (arm motion noise) is separated.

An adaptive filter coefficient of the adaptive filter 31 is updated by an adaptive algorism 34 and the IIR filter 32 on a basis of the first body motion analysis result. For example, in a case where the adaptive algorism 34 is an NLMS algorism, a parameter or the like which decides an amount of update of the adaptive filter coefficient called a step size is controlled on the basis of the first body motion analysis result, for example. As a result, a convergence time for obtaining an optimal coefficient is improved, which makes it possible to follow a change in body motion frequency.

Further, in the adaptive filter 31, in order to separate the body motion noise (false signal) included in the observation signal, it is desirable that a correlation of the input signal and the body motion noise be higher. In this embodiment, as shown in FIG. 6, an influence of a body motion to a bloodstream is modeled to obtain a noise model 35. A transfer function (FIR filter coefficient) of the body motion to the bloodstream is calculated and recorded in advance. To the adaptive filter 31, a result of the FIR filter process with respect to the body motion signal is input. That is, the body motion signal is not used as an input signal, but the FIR filter process result is used as the input signal. As a result, the convergence time for obtaining an optimal coefficient at a time when the body motion intensity and the body motion frequency are changed is improved.

The transfer function of the noise model 35 depends on conditions or the like of blood vessels and bloodstream, so the optimal coefficient exists for each user. Therefore, in this embodiment, at a time when a user uses the heart rate measurement apparatus 100, a process of obtaining a transfer function of the body motion to the bloodstream as the noise model 35.

Figure 7:
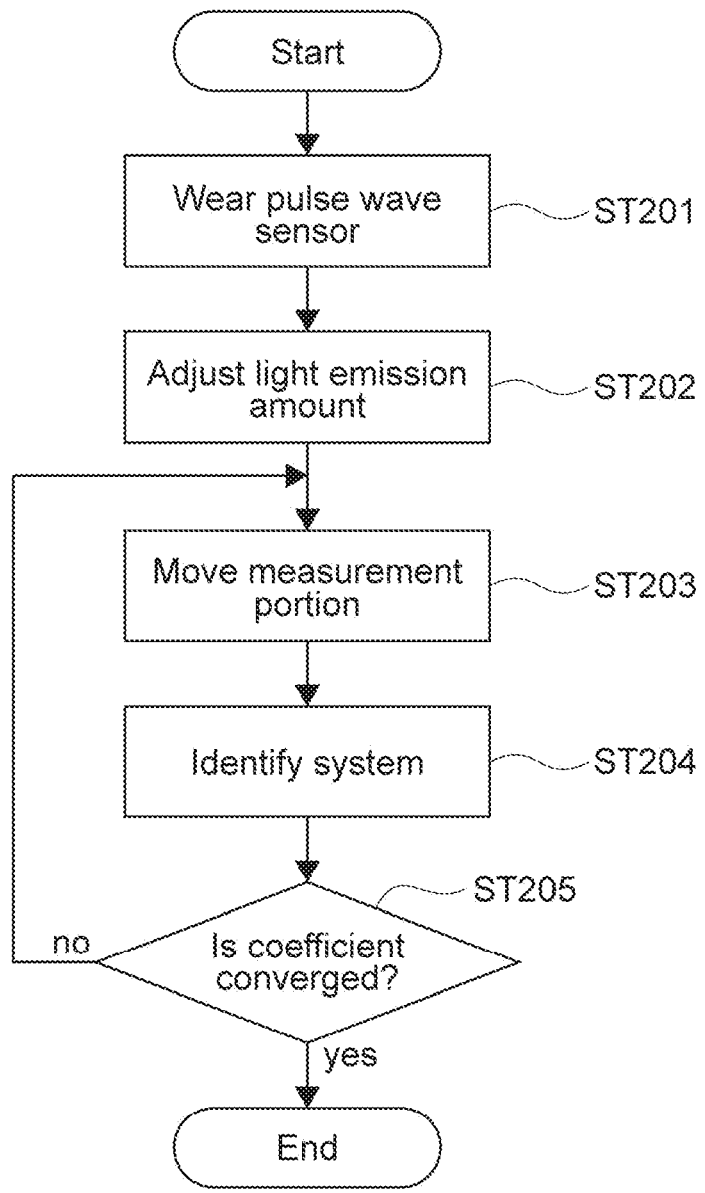
FIG. 7 A flowchart showing a calculation example of a transfer function.

FIG. 7 is a flowchart showing a calculation example of the transfer function. First, the first PPG sensor 12 is put on a measurement portion (Step 201). A return light quantity differs between individuals due to color of skin or the like on the measurement portion, so the light quantity of the first light emission unit of the first PPG sensor 12 is controlled so as not to cause the pulse wave signal to be saturated in a resting state (Step S202).

The user is urged to move the measurement portion. Specifically, to the measurement portion, an impulsive body motion is given in an artery bloodstream direction (see, FIG. 1B), and the pulse wave signal and the body motion signal are measured (Step 203). By the first noise reduction processing unit 30, the input signal is set as the body motion signal by the impulsive body motion, the output signal is set as the pulse wave signal, and system identification is performed by the adaptive filter 31 (Step S204).

It is determined whether the transfer function (FIR filter coefficient) is converged or not (Step 205). In a case where it is determined that the transfer function is not converged (No in Step 205), the process returns to Step S203. In a case where the transfer function is converged (Yes in Step 205), the process is terminated.

It should be noted that the description is given above by using the case of the transfer function (FIR filter coefficient) of the body motion to the bloodstream as the noise model 35. As another embodiment, approximation by an N-order polynomial can be considered. For example, by using a least-squares method or the like, a coefficient of the N-order polynomial may be calculated.

Further, the obtained adaptive filter coefficient is subjected to the IIR filter process by the IIR filter 32. For example, a past value of a preceding sample is set as 0 (zero). In a case where it is determined as a resting state, the IIR filter process is set to ON, thereby setting the adaptive filter process to OFF. At a time of a movement, a feedback factor is set as 0.0, and the IIR filter process is set to OFF, with the result that the adaptive filter process is set to ON. With this configuration, only by controlling the feedback factor of the IIR filter 32 in accordance with the first body motion analysis result, it is possible to smoothly switch existence or nonexistence of the adaptive filter process.

Thanks to the devices described above, even if abrupt changes in the body motion intensity and the body motion frequency occur, the convergence time of the adaptive filter process is improved, and thus a noise reduction effect can be sufficiently obtained.

Figure 8:
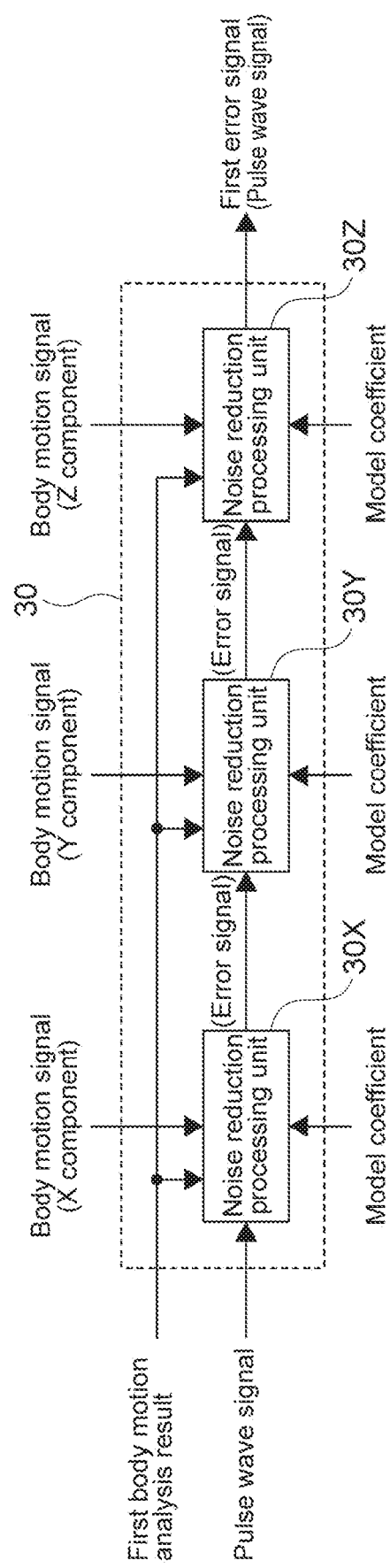
FIG. 8 A block diagram showing a configuration example of a first noise reduction processing unit in a case where an acceleration sensor is a triaxial acceleration sensor.

FIG. 8 is a block diagram showing a configuration example of the first noise reduction processing unit 30 in a case where the acceleration sensor 14 is the triaxial acceleration sensor. A transfer function of each component of the triaxial acceleration with respect to the bloodstream may be calculated in advance, and a cascade connection is performed for noise reduction processing units 30X, 30Y, and 30Z with respect to XYZ acceleration components.

For example, to the noise reduction processing unit 30X, a model coefficient, an X component of the body motion signal, the first body motion analysis result, and a pulse wave signal before the noise reduction process are input. To the noise reduction processing unit 30Y, the model coefficient, the Y component of the body motion signal, the first body motion analysis result, and an output (error signal) of the noise reduction processing unit 30X are input. To the noise reduction processing unit 30Z, the model coefficient, the Z component of the body motion signal, the first body motion analysis result, and an output (error signal) of the noise reduction processing unit 30Y are input. The output (error signal) of the noise reduction processing unit 30Z is the first error signal.

As shown in FIG. 2, in this embodiment, the first error signal and the reliability thereof are calculated. For example, a temporal change of the adaptive filter coefficient is analyzed, and thus whether the arm motion noise reduction process is appropriately analyzed or not. Thus, the reliability of the output first error signal is output as a parameter. For example, a total of temporal subtraction absolute values of filter coefficients is calculated. In a case where an abrupt change in the coefficients occurs, or in a case of being a threshold value or more, it is determined that the reliability is low, or there is no reliability. The method of calculating the reliability is not limited, and another method may be used. Further, the reliability output from the body motion analysis unit 20 based on the light quantity of the first PPG sensor 12 may be used as appropriate.

The reference signal generation unit 50 shown in FIG. 2 generates a reference signal for separating a body motion noise (hereinafter, referred to as finger and wrist motion noise) caused due to a motion of a finger and a wrist (Step 104). It is desirable that a correlation of the reference signal and the finger and wrist motion noise be higher. In this embodiment, the reference signal is generated on a basis of the pulse wave signal from the first PPG sensor 12, the reference pulse wave signal from the second PPG sensor 13, and the body motion signal from the acceleration sensor 14.

For example, the pulse wave signal and the reference pulse wave signal are respectively subjected to a main component analysis, and a noise signal is selected from the generated two signals. In the PPG system, a body motion noise component is stronger than a signal component, so a separated signal having a stronger power is a signal having a higher correlation with the finger and wrist motion noise. The signal is used as the reference signal. In addition, the method of generating the reference signal is not limited. As the reference signal, a signal obtained by synthesizing the pulse wave signal and the reference pulse wave signal, a signal based on only the pulse wave reference signal, or the like may be used. Further, the pulse wave reference signal itself may be used as the reference signal.

The second noise reduction processing unit 40 performs a reduction process of the finger and wrist motion noise (Step 105). It should be noted that in the figure, the second noise reduction processing unit 40 is referred to as a finger and wrist motion noise reduction processing unit 40.

Figure 9:
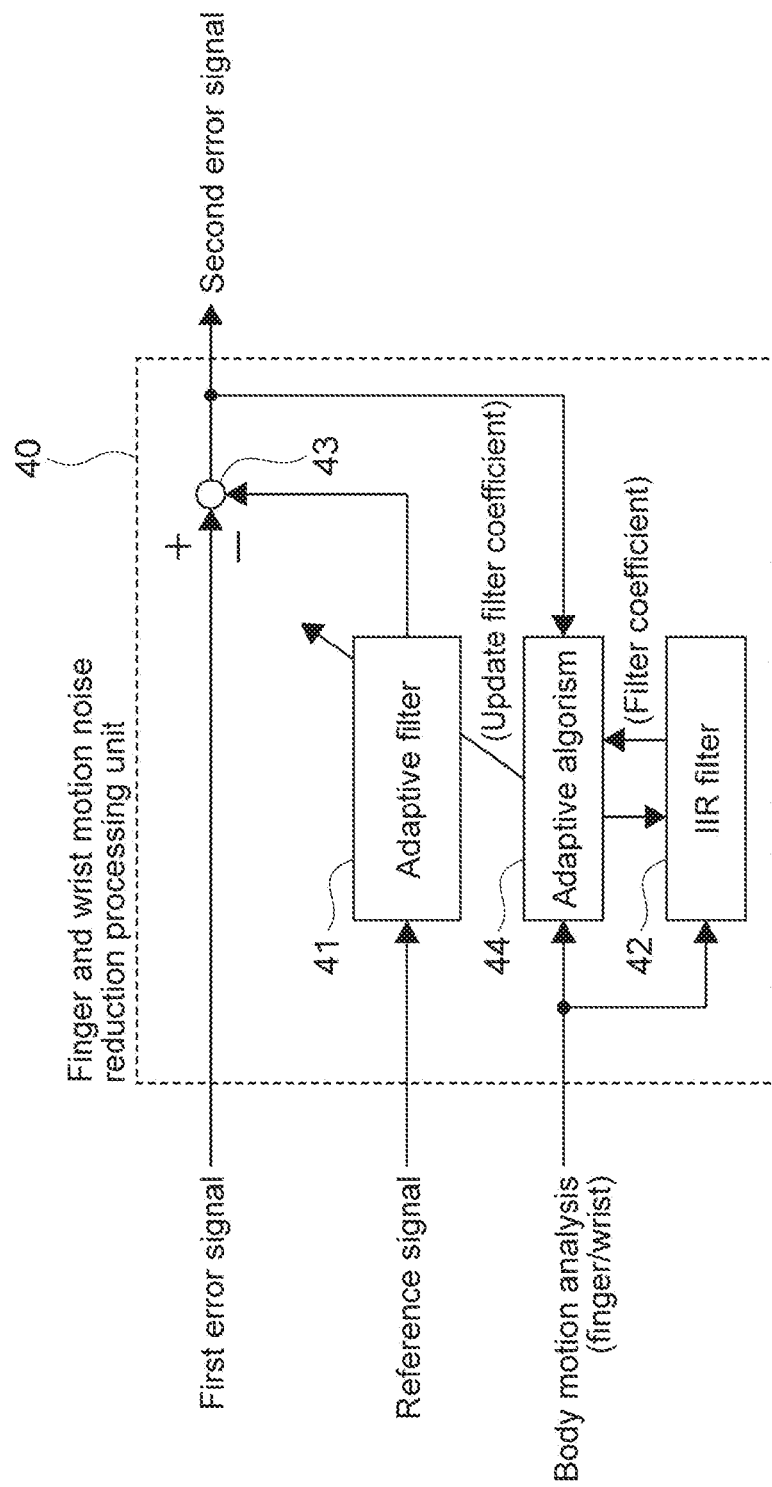
FIG. 9 A block diagram showing a configuration example of a second noise reduction processing unit.

FIG. 9 is a block diagram showing a configuration example of the second noise reduction processing unit 40. The second noise reduction processing unit 40 includes an adaptive filter 41 (second adaptive filter), an IIR filter 42, and a subtractor 43. An input signal of the adaptive filter 41 is the reference signal. An observation signal is the first error signal (pulse wave signal) output from the first noise reduction processing unit 30. The subtractor 43 subtracts an output value of the adaptive filter 41 from the first error signal, to output the second error signal. The second error signal corresponds to the pulse wave signal from which the body motion noise (finger and wrist motion noise) is separated.

The adaptive filter coefficient of the adaptive filter 41 is updated by an adaptive algorism 44 and the IIR filter 42 on a basis of the second body motion analysis result. As a result, the convergence time for obtaining the optimal coefficient is improved, which makes it possible to follow a change in the body motion frequency.

Further, like the first noise reduction processing unit 30, the obtained adaptive filter coefficient is subjected to the IIR filter process by the IIR filter 42. Therefore, only by controlling a feedback factor of the IIR filter 42 in accordance with the second body motion analysis result, it is possible to smoothly switch the existence or nonexistence of the adaptive filter process.

With the second error signal, a reliability thereof is calculated. For example, by analyzing a temporal change of the adaptive filter coefficient, whether the arm motion noise reduction process appropriately functions or not is analyzed, and the reliability of the second error signal to be output is output as a parameter. For example, a total of the temporal subtraction absolute values of the respective filter coefficients is calculated. In a case where an abrupt coefficient change occurs, or in a case of being a threshold value or more, it is determined that the reliability is low, or there is no reliability. The method of calculating the reliability is not limited, another method may be provided. Further, the reliability based on the light quantity of the second PPG sensor 13 output from the body motion analysis unit 20 may be used as appropriate.

On a basis of the pulse wave signal (second error signal) output from the second noise reduction processing unit 40, a heart rate variability and a heart rate trend are detected (Step 106). The heart rate variability is detected by the heart rate variation detection unit 60 shown in FIG. 2. Further, the heart rate trend is detected by the heart rate trend detection unit 70 shown in FIG. 2.

Figure 10:
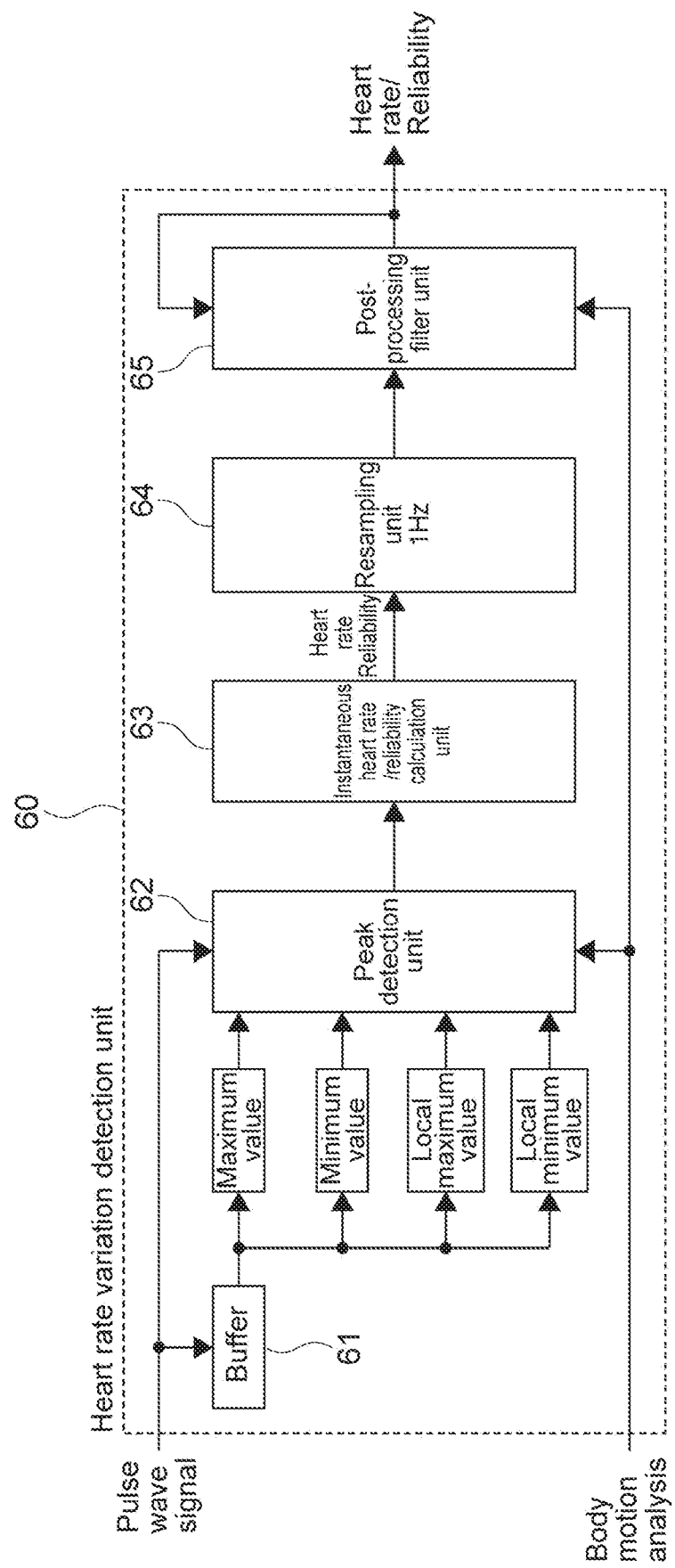
FIG. 10 A block diagram showing a configuration example of heart rate variation detection unit.

FIG. 10 is a block diagram showing a configuration example of the heart rate variation detection unit 60. The heart rate variation detection unit 60 includes a buffer 61, a peak detection unit 62, an instantaneous heart rate/reliability calculation unit 63, a resampling unit 64, and a post-processing filter unit 65.

In this embodiment, the peak detection unit 62 detects a peak position by pulsation from the pulse wave signal from which the body motion noise is reduced. As shown in FIG. 10, to the peak detection unit 62, through the buffer 61, a maximum value, a minimum value, a local maximum value, and a local minimum value of the pulse wave signal are input. Hereinafter, an example of a peak position detection by a local maximum value detection will be described.

There is a case where a contact state of the first PPG sensor 12 may be changed due to a body motion, and the intensity of the pulse wave signal may be modulated. At this time, if a peak detection is performed by using a fixed threshold value set in advance, it may be impossible to detect the peak position by the pulsation. Further, there is a fear that a false peak by the body motion noise may be erroneously detected as a peak by the pulsation.

In this embodiment, so as not to cause a detection error as described above, as indicated by the following expression, a threshold value th of the peak intensity is decided from a maximum value vmax and a minimum value vmin of the pulse wave signal in a certain analysis window.

$$th = v\,min + \alpha \cdot (v\,max - v\,min)$$

$$0 < \alpha < 1$$

As a result, in accordance with the intensity of the pulse wave signal, the threshold value th of the peak intensity is adaptively controlled. Thus, it is possible to detect the peak position even when the intensity of the pulse wave signal is modulated.

It should be noted that even in a case where the threshold value process as described above is performed, due to remaining of a body motion noise whose frequency is low, a local maximum value (broad local maximum value) having a strong peak intensity but a small projection degree may be erroneously detected as a peak by the pulsation.

In view of this, in this embodiment, one or a plurality of process examples described below are combined and executed.

From a preceding local minimum value and a local maximum value, a current projection degree of the local maximum value, specifically, a level difference is calculated, and a threshold value determination is performed.

In consideration of the modulation of the pulse wave intensity by the body motion, the threshold value described above is adaptively controlled in accordance with the first and/or second body motion analysis result.

A range from which the local maximum value is detected is limited with the heart rate obtained by the heart rate trend detection unit 70 as a center of a search range. In this case, the heart rate variation detection unit 60 and the heart rate trend detection unit 70 may be subjected to a cascade connection.

For example, by performing the processes described above, it is possible to reduce the erroneous detection of a false peak due to a body motion noise which cannot be removed by the first and second noise reduction processing units 30 and 40. As a result, accuracy of an instantaneous heart rate by the heart rate variation detection unit 60 is improved.

The instantaneous heart rate/reliability calculation unit 63 calculates an instantaneous heart rate and a reliability. The instantaneous heart rate means a momentary heart rate, for example, a value obtained by multiplying an inverse number of a time interval of a peak position (position of local maximum value) by 60 (seconds) is calculated. The instantaneous heart rate is calculated, for example, with the result that in a heart rate training or the like, the heart rate variability can be measured in real time with high accuracy.

It should be noted that the "heart rate" is a number of times of heart beats at a time of pumping blood throughout a body generally, and the "pulse rate" is a number of times of pulsations generated in an artery. As long as arrhythmia, a pulse deficit, or the like is not found, the "heart rate" and the "pulse rate" are substantially the same. In the present disclosure, a measurement result obtained by the heart rate measurement apparatus 100 is described as the heart rate variability, the heart rate trend, the instantaneous heart rate, or the like. Instead of those, it is also possible to describe the result as a pulse rate variability, a pulse rate trend, an instantaneous pulse rate, or the like. Of course, the present technology can also be applied to a case where the "pulse rate", which is the pulsation of an artery of the measurement portion is treated as a parameter different from the "heart rate".

The reliability is calculated on a basis of a level difference between a local maximum value and a local minimum value, for example. As the level difference between a local maximum value detected as a peak value and a preceding local minimum value (or immediately after that), that is, as a projection degree of the local maximum value is larger, a higher reliability is given. By another method, the reliability may be calculated.

The resampling unit 64 performs resampling to 1 Hz, and after that, the post-processing filter unit 65 performs post-processing. For example, as the post-processing filter unit 65, an IIR filter and a feedback factor calculation unit are configured, and a feedback factor of the IIR filter is controlled as appropriate.

For example, there is a case where the first and second noise reduction processing units 30 and 40 and the peak detection unit 62 cannot completely remove the noise, and an abnormal value of a temporal change of the instantaneous heart rate is caused. Generally, the instantaneous heart rate has a significantly high correlation with time. In view of this, in a case where the temporal change of the instantaneous heart rate is larger than a threshold value set in advance, the feedback factor of the IIR filter of the post-processing filter unit 65 is controlled to be larger (for example, value close to 1.0). As a result, it is possible to modify (reduce) erroneous detection by performing an extrapolation process for a past instantaneous heart rate as it is. Further, on a basis of an analysis result from the body motion analysis unit 20, the feedback factor of the IIR filter is controlled to be a value smaller than 1.0, for example, approximately 0.5 during a movement of a user. As a result, it is possible to stabilize the instantaneous heart rate.

Figure 11:
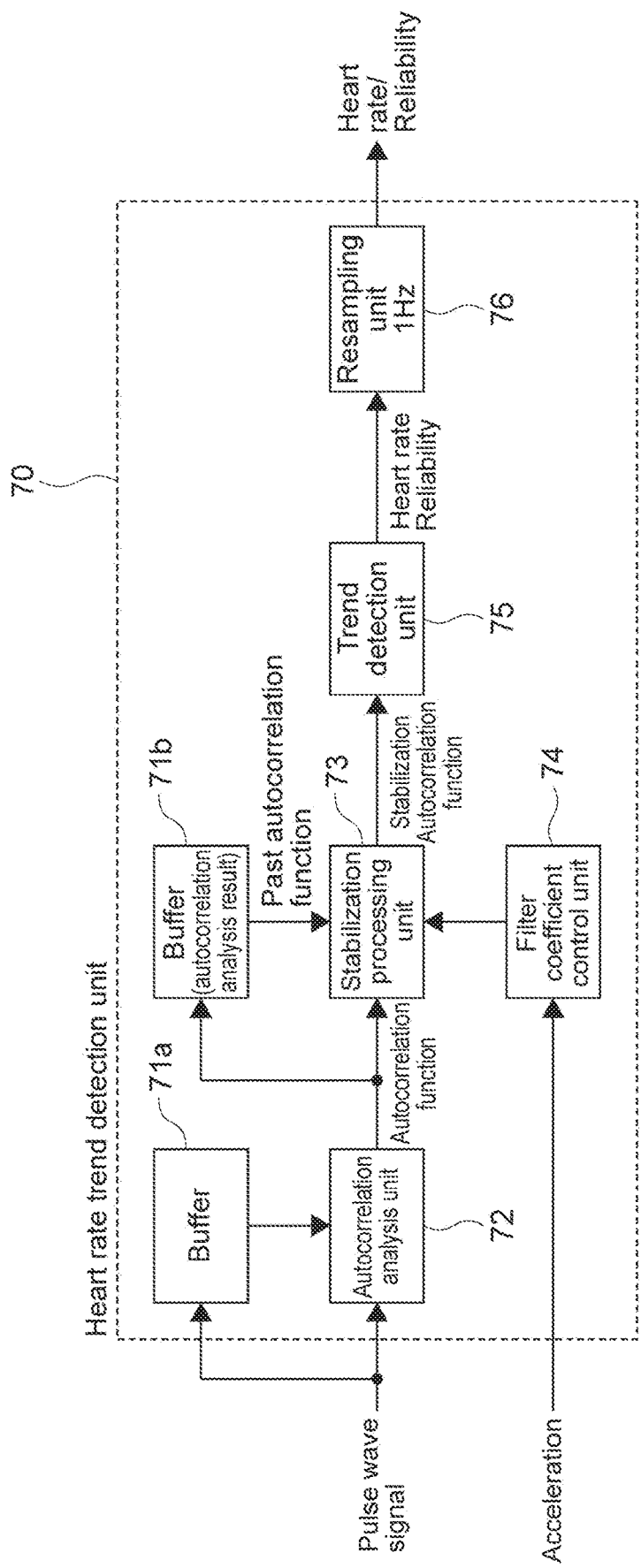
FIG. 11 A block diagram showing a configuration example of heart rate trend detection unit.

FIG. 11 is a block diagram showing a configuration example of the heart rate trend detection unit 70. The heart rate trend detection unit 70 includes buffers 71$a$ and 71$b$, an autocorrelation analysis unit 72, a stabilization processing unit 73, a filter coefficient control unit 74, a trend detection unit 75, and a resampling unit 76.

The autocorrelation analysis unit 72 performs an autocorrelation analysis with respect to the pulse wave signal from which the body motion noise is reduced, for each one sampling time. There are various methods of calculating the autocorrelation function. In this embodiment, an analysis using a normalized autocorrelation function is performed.

The stabilization processing unit 73 performs weighting addition of a past autocorrelation function held in the buffer 71$b$ to an autocorrelation function at a current time, with the result that the autocorrelation function is stabilized. A weighting parameter is determined from an acceleration signal (body motion signal) by the filter coefficient control unit 74.

The trend detection unit 75 detects lag $\tau$, autocorrelation value of which is higher from the stabilized autocorrelation function continuously, and a cycle of the pulse wave signal is calculated as the heart rate trend. On a basis of the heart rate trend, the heart rate and the reliability thereof is calculated. It should be noted that the heart rate is calculated on a basis of the heart rate trend (cycle of pulse wave signal) and is different from the instantaneous heart rate.

The reliability is calculated on a basis of, for example, a normalized autocorrelation value on a position of a specified lag $\tau$, that is, an autocorrelation value in the detected cycle. As the autocorrelation value is higher, a higher reliability is given. The reliability may be calculated by another method. After the resampling unit 76 performs resampling to 1 Hz, the heart rate and the reliability thereof are output.

The heart rate variation detection unit 60 and the heart rate trend detection unit 70 correspond to a plurality of calculation units that calculate heart rate candidate information with the reliability on a basis of the pulse wave signal in this embodiment. Further, those detection units can be referred to as a heart rate estimator. Further, the instantaneous heart rate obtained by the peak detection and the heart rate obtained by the autocorrelation analysis respectively correspond to the heart rate candidate information.

The number of calculation units that calculate the heart rate candidate information on a basis of the pulse wave signal, an algorism for the calculation, and the like are not limited and may be set as appropriate. Further, as the heart rate candidate information, typically, the heart rate is calculated, but other information may be calculated.

The integration processing unit 80 shown in FIG. 2 performs an integration process (Step 107). Specifically, on a basis of the instantaneous heart rate and the heart rate and the reliability thereof output from the heart rate variation detection unit 60 and the heart rate trend detection unit 70, respectively, as the heart rate candidate information, the heart rate information is output. That is, the integration processing unit 80 outputs ultimate heart rate information from output results of a plurality of heart rate estimators and reliabilities thereof. The integration processing unit 80 functions as an output unit in this embodiment.

As a method of outputting the ultimate heart rate information, for example, heart rate candidate information with a highest reliability is output. That is, the reliability of the instantaneous heart rate and the reliability of the heart rate based on the heart rate trend are compared. Then, the heart rate with a higher reliability is output as the ultimate heart rate information.

Alternatively, the reliabilities calculated by the plurality of heart rate estimators may be changed into multi-dimensional vectors, and thus the ultimate heart rate information (heart rate) may be calculated by a discriminator or the like configured by a neural network. In a case where the neural network is configured, for example, a heart rate measured by an electrocardiograph or the like is correct data. At the same time, from the plurality of measured pulse wave signals (pulse wave signal and reference pulse wave signal) and the acceleration signal (body motion signal), a coefficient of the neural network may be obtained by machine learning with the multi-dimensional vectors calculated by the plurality of heart rate estimators as input data.

Further, in this embodiment, the integration processing unit 80 determines whether fallback is performed or not. For example, in a case where the reliability of the instantaneous the heart rate and the reliability of the heart rate based on the heart rate trend are lower than a predetermined threshold value, the fallback is performed. As the fallback, for example, a preceding heart rate is pre-held and output as the ultimate heart rate information. As a result, while preventing an output of the heart rate information with a low reliability, the heart rate measurement can be continued. It should be noted that the specific operation of the fallback is not limited.

Further, on a basis of the reliabilities calculated by the first and second noise reduction processing units 30 and 40, whether the fallback operation is required or not may be determined. For example, in a case where the reliabilities calculated in the first and second noise reduction processing units 30 and 40 and the reliabilities calculated in the heart rate variation detection unit 60 and the heart rate trend detection unit 70 are low, the fallback is performed. Alternatively, in a case where the reliabilities calculated in the first and second noise reduction processing units 30 and 40 are low, irrespective of values of the reliabilities calculated by the two heart rate estimators, the fallback is performed. Further, in a case where the reliabilities calculated in the first and second noise reduction processing units 30 and 40 are high, even if the reliabilities calculated by the two heart rate estimators are low, the fallback is not performed, and the heart rate candidate information with the higher reliability is output. This process can be achieved.

There is a case where a body motion causes a reduction in intimate contact between the first and second PPG sensors 12 and 13 and a skin, and outside light and stray light is mixed, resulting in saturation of the pulse wave signal. Further, there is a case where a change in shape of an arm caused by a body motion causes a change in return light quantity, resulting in a saturation of the pulse wave signal. To avoid those cases, a light quantity of a light emission element (light emission unit) may be dynamically controlled to achieve an appropriate return light quantity. As a result of controlling the light quantity, in a case where the reliability of the pulse wave signal is low, or in a case where there is no reliability, the fallback may be performed. In addition, on a basis of the reliability calculated by the body motion analysis unit 20 or the autocorrelation analysis value calculated by the heart rate trend detection unit 70, whether the fallback operation is necessary or not may be determined.

The stabilization processing unit 90 stabilizes the output heart rate as the ultimate heart rate information. For example, an erroneous detection of the instantaneous heart rate due to the body motion noise which cannot be removed by the first and second noise reduction processing units 30 and 40 and the peak detection is reduced. A specific configuration or the like of the stabilization processing unit 90 is not limited.

As described above, in the heart rate measurement apparatus 100 according to this embodiment, the heart rate variation detection unit 60 and the heart rate trend detection unit 70 which function as the plurality of calculation units each calculate the heart rate candidate information with the reliability. Therefore, on the basis of the information, it is possible to ultimately output the heart rate information with the high reliability. As a result, it is possible to achieve a highly accurate heart rate measurement.

In the peak detection by the heart rate variation detection unit 60, it is possible to detect the peak position by using the pulsation, so the heart rate variability can be detected with high accuracy. On the other hand, in the autocorrelation analysis by the heart rate trend detection unit 70, a periodicity of the pulse wave is used. Therefore, it is difficult to detect the heart rate variability with high accuracy. However, in the autocorrelation analysis, it is possible to sufficiently suppress a possibility of an erroneous detection of a peak caused by a residual noise as the peak position caused by the pulsation, which exhibits a very high noise resistance. In this way, the plurality of heart rate estimators having different features are prepared, and on a basis of the respective reliabilities, the ultimate heart rate information is calculated. As a result, it is possible to achieve the heart rate detection while making up for such shortcomings of each other. Thus, as compared to a case a single heart rate estimator is used, a significantly highly accurate heart rate measurement is achieved.

Further, the heart rate sensor of the PPG system can measure the pulse wave signal in a rest state with relatively high accuracy. However, when the measurement portion is moved, a body motion noise is generated in the observation signal. Examples of a factor of the body motion noise in a wristband type heart rate sensor include mixing of an unnecessary skin surface reflection due to a change in a contact state between the PPG sensor and the measurement portion, mixing of outside light transmitted underneath a skin, and the like. Further, even in a case where the contact state between the PPG sensor and the measurement portion is good, examples of the factor include a fact that a false signal is generated due to a bloodstream variation caused by moving the measurement portion, a variation of a light absorption amount due to deformation of a tissue under a skin associated with a motion of a finger and a wrist (motion of bone), and the like. For example, if a false peak signal is mixed into the pulse wave signal due to complex factors described above, it becomes difficult to determine which peak is a peak signal caused by the pulsation. As a result, in a case where the instantaneous heart rate is calculated from a temporal difference between the peak positions, there is a fear in that an erroneous pulse rate may be calculated.

As a method of reducing the body motion noise as described above, the adaptive filter described above is effective. The adaptive filter will be described again. The adaptive filter means a method of automatically calculating a filter coefficient (W) which minimizes an error signal (e) power at a time when an observation signal (d) and an input signal (X) are given. In a case where the observation signal is set as the pulse wave signal, it is possible to separate a noise which is mixed into observation signal by referring to a signal having a high correlation with the noise as the input signal.

In the heart rate measurement apparatus 100 according to this embodiment, the first noise reduction processing unit 30 reduces the arm motion noise, and the second noise reduction processing unit 40 reduces the finger and wrist motion noise. Therefore, it is possible to sufficiently reduce a noise caused by a periodical motion of arms represented by walking or running and a noise caused by a non-periodical motion such as motions of fingers and wrists. As a result, it is possible to measure the heart rate variability in daily life at all times with high accuracy.

As a method of stably calculating the pulse rate, a frequency analysis method is also known. For example, a frequency analysis is performed for a pulse wave signal that has been subjected to the noise reduction process. A frequency with a maximum spectrum intensity is determined as a pulse wave number. However, in the frequency analysis method, there is a problem in estimation accuracy of the heart rate variability in a low heart rate area in principle. In the heart rate measurement apparatus 100 according to this embodiment, it is possible to calculate the heart rate variability in the low heart rate area with high accuracy.

In this embodiment, as an embodiment of the biological information processing apparatus according to the present technology, the heart rate measurement apparatus 100 is described. The embodiment of the biological information processing apparatus according to the present technology is not limited to this and includes an arbitrary apparatus provided with a sphygmographic sensor. For example, an arbitrary electronic apparatus including various wearable apparatuses such as a headband type, a neckband type, and a belt type, an arbitrary personal digital assistant (PDA) such as a smart phone and a tablet terminal, medical equipment, a game machine, a home electric apparatus, and the like, can be configured as the biological information processing apparatus according to the present technology.

Further, a wearable apparatus, a mobile apparatus, or the like having only a function of the controller 15 shown in FIG. 1B may be configured as the information processing apparatus according to the present technology. In this case, an interface or the like connected with the sphygmographic sensor functions as an obtaining unit which obtains the pulse wave signal.

<Other Embodiments>

The present technology is not limited to the embodiment described above, various other embodiments can be achieved.

In the above description, to generate the pulse wave signal, the first PPG sensor 12 is provided. To generate the reference pulse wave signal for generating the reference signal, the second PPG sensor 13 is provided. Instead of this, any one of the pulse wave candidate signals output from the first and second PPG sensors 12 and 13 is selected as appropriate, and the signal may be output as the pulse wave signal as a subject of calculation of the heart rate.

For example, at a time when the return light quantities of the two pulse wave candidate signals output from the first and second PPG sensors 12 and 13 are set to be uniform, the signal having a stronger pulse wave component is selected as a main signal, and a noise reduction process subsequent thereto is performed for the pulse wave candidate signal as a subject. That is, as a plurality of sphygmographic sensors, the first sphygmographic sensor for generating the pulse wave signal as a subject of the noise reduction process may be determined in advance, or the first sphygmographic sensor may be selected as appropriate from among the sphygmographic sensors. By selecting the first sphygmographic sensor in each case, the signal having the strongest pulse wave component can be selected. Thus, the highly accurate heart rate measurement is achieved.

At least two of the feature parts according to the present technology described above can be combined. That is, various feature parts described in the embodiments may be arbitrarily combined irrespective of the embodiments. Further, the various effects described above are merely examples and are not limited, and other effects may be exerted.

It should be noted that the present technology can take the following configurations.

(1) A biological information processing apparatus, including:

a sphygmographic sensor unit that outputs a pulse wave signal;

a plurality of calculation units that respectively calculate heart rate candidate information with a reliability on a basis of the output pulse wave signal; and an output unit that outputs heart rate information on a basis of the heart rate candidate information and the reliability thereof calculated by each of the plurality of calculation units.

(2) The biological information processing apparatus according to (1), further including:

a body motion sensor that outputs a body motion signal; and a noise reduction processing unit that separates a body motion noise from the pulse wave signal output from the sphygmographic sensor unit on a basis of the body motion signal, in which the plurality of calculation units respectively calculate the heart rate candidate information and the reliability thereof on a basis of the pulse wave signal from which the body motion noise is separated.

(3) The biological information processing apparatus according to (2), in which the plurality of calculation units include a first calculation unit that detects a peak position of the pulse wave signal and calculates an instantaneous heart rate on a basis of the pulse wave signal from which the body motion noise is separated.

(4) The biological information processing apparatus according to (3), in which the first calculation unit calculates a reliability of the instantaneous the heart rate on a basis of a difference between a local maximum value and a local minimum value of the pulse wave signal.

(5) The biological information processing apparatus according to (3) or (4), in which the plurality of calculation units include a second calculation unit that detects a period of the pulse wave signal by an autocorrelation analysis and calculates a heart rate on a basis of the pulse wave signal from which the body motion noise is separated.

(6) The biological information processing apparatus according to (5), in which the second calculation unit calculates a reliability of the heart rate on a basis of an autocorrelation value in the detected period.

(7) The biological information processing apparatus according to any one of (2) to (6), in which the sphygmographic sensor unit includes a plurality of sphygmographic sensors, and outputs any one of a plurality of pulse wave candidate signals generated by the plurality of sphygmographic sensors as the pulse wave signal.

(8) The biological information processing apparatus according to (7), in which the noise reduction processing unit includes a first adaptive filter to which the body motion signal that is subjected to a filter process by a transfer function calculated by modeling an influence of a body motion on a bloodstream is input as an input signal, and outputs a first error signal obtained by subtracting an output value of the first adaptive filter from the pulse wave signal output from the sphygmographic sensor unit.

(9) The biological information processing apparatus according to any one of (7) to (9), further including:

a generation unit that generates a reference signal for separating the body motion noise on a basis of the plurality of pulse wave candidate signals generated by the plurality of sphygmographic sensors, in which the noise reduction processing unit includes a second adaptive filter to which the reference signal is input as an input signal, and outputs a second error signal obtained by subtracting an output value of the second adaptive filter from the first error signal.

(10) The biological information processing apparatus according to (9), in which the plurality of sphygmographic sensors include a first sphygmographic sensor that generates the pulse wave signal, and a second sphygmographic sensor that generates a reference pulse wave signal for generation of the reference signal.

(11) The biological information processing apparatus according to (10), in which the first sphygmographic sensor includes a first light emission unit that emits light in a first wavelength range and a first light reception unit that detects reflection light of the light in the first wavelength range, and the second sphygmographic sensor includes a second light emission unit that emits light in a second wavelength range longer than the first wavelength range and a second light reception unit that detects reflection light of the light in the second wavelength range.

(12) The biological information processing apparatus according to (10) or (11), further including:
a body motion analysis unit that detects a body motion variation by analyzing the body motion signal, and outputs the detected variation as a first body motion analysis result, in which
the noise reduction processing unit updates an adaptive filter coefficient in the first adaptive filter on a basis of the output first body motion analysis result.

(13) The biological information processing apparatus according to (12), in which
the body motion analysis unit detects a body motion variation by analyzing the reference pulse wave signal, and outputs the detected variation as a second body motion analysis result, and
the noise reduction processing unit updates an adaptive filter coefficient in the second adaptive filter on a basis of the output second body motion analysis result.

(14) The biological information processing apparatus according to any one of (1) to (13), in which
the output unit outputs the heart rate candidate information with a highest reliability as the heart rate information.

(15) The biological information processing apparatus according to any one of (1) to (14), in which
the output unit determines whether fallback is performed or not on a basis of reliability calculated by each of the plurality of calculation units.

(16) The biological information processing apparatus according to (15), in which
the output unit determines whether the fallback is performed or not on a basis of a reliability calculated with a pulse wave signal from which a body motion noise is separated.

REFERENCE SIGNS LIST 10 sensor main body unit
12 first PPG sensor
13 second PPG sensor
14 acceleration sensor
15 controller
20 body motion analysis unit
30 first noise reduction processing unit
31, 41 adaptive filter
35 noise model
40 second noise reduction processing unit
50 reference signal generation unit
60 heart rate variation detection unit
62 peak detection unit
63 reliability calculation unit
70 heart rate trend detection unit
72 autocorrelation analysis unit
75 trend detection unit
80 integration process unit
100 heart rate measurement apparatus

The invention claimed is:

1. A biological information processing apparatus, comprising:
a plurality of sphygmographic sensors configured to generate a plurality of pulse wave candidate signals;
a body motion sensor configured to output a body motion signal;
a first adaptive filter;
a second adaptive filter; and
a central processing unit (CPU) configured to:
generate a reference signal based on the plurality of pulse wave candidate signals;
calculate a transfer function based on a model of an influence of a body motion on a bloodstream;
execute a filter process on the body motion signal based on the calculated transfer function;
input, to the first adaptive filter, the body motion signal on which the filter process is executed;
output a first signal by subtraction of an output value of the first adaptive filter from a pulse wave signal, wherein
the pulse wave signal corresponds to a pulse wave candidate signal of the plurality of pulse wave candidate signals, and
the first signal corresponds to the pulse wave signal from which a body motion noise is separated;
input the reference signal to the second adaptive filter;
output a second signal by subtraction of an output value of the second adaptive filter from the first signal;
calculate, based on the pulse wave signal from which the body motion noise is separated, heart rate candidate information and a reliability of the heart rate candidate information; and
output heart rate information based on the heart rate candidate information and the reliability of the heart rate candidate information.

2. The biological information processing apparatus according to claim 1, wherein the CPU is further configured to:
detect a peak position of the pulse wave signal; and
calculate an instantaneous heart rate based on the pulse wave signal from which the body motion noise is separated.

3. The biological information processing apparatus according to claim 2, wherein the CPU is further configured to calculate a reliability of the instantaneous heart rate based on a difference between a local maximum value and a local minimum value of the pulse wave signal.

4. The biological information processing apparatus according to claim 2, wherein the CPU is further configured to:
execute an autocorrelation analysis on the pulse wave signal;
detect a period of the pulse wave signal based on the autocorrelation analysis; and
calculate a heart rate based on the pulse wave signal from which the body motion noise is separated.

5. The biological information processing apparatus according to claim 4, wherein the CPU is further configured to calculate a reliability of the heart rate based on an autocorrelation value in the detected period.

6. The biological information processing apparatus according to claim 1, wherein the plurality of sphygmographic sensors includes:
a first sphygmographic sensor configured to generate the pulse wave signal, and
a second sphygmographic sensor configured to generate a reference pulse wave signal for the generation of the reference signal.

7. The biological information processing apparatus according to claim 6, wherein
the first sphygmographic sensor includes a first light emitter configured to emit light in a first wavelength range and a first photodetector configured to detect reflection light of the light in the first wavelength range, and
the second sphygmographic sensor includes a second light emitter configured to emit light in a second wavelength range longer than the first wavelength range and a second photodetector configured to detect reflection light of the light in the second wavelength range.

8. The biological information processing apparatus according to claim 6, wherein the CPU is further configured to:
    analyze the body motion signal;
    detect a first body motion variation based on the analysis of the body motion signal;
    output the detected first body motion variation as a first body motion analysis result; and
    update an adaptive filter coefficient in the first adaptive filter based on the output first body motion analysis result.

9. The biological information processing apparatus according to claim 8, wherein the CPU is further configured to:
    analyze the reference pulse wave signal;
    detect a second body motion variation based on the analysis of the reference pulse wave signal;
    output the detected second body motion variation as a second body motion analysis result; and
    update an adaptive filter coefficient in the second adaptive filter based on the output second body motion analysis result.

10. The biological information processing apparatus according to claim 1, wherein the CPU is further configured to:
    calculate, based on the pulse wave signal from which the body motion noise is separated, first heart rate candidate information and a reliability of the first heart rate candidate information;
    calculate, based on the pulse wave signal from which the body motion noise is separated, second heart rate candidate information and a reliability of the second heart rate candidate information; and
    output the first heart rate candidate information as the heart rate information based on the reliability of the first heart rate candidate information that is higher than the reliability of the second heart rate candidate information.

11. The biological information processing apparatus according to claim 1, wherein the CPU is further configured to determine, based on the reliability of the heart rate candidate information, execution of fallback.

12. The biological information processing apparatus according to claim 11, wherein the CPU is further configured to:
    calculate a reliability of the pulse wave signal from which the body motion noise is separated; and
    determine, based on the reliability of the pulse wave signal from which the body motion noise is separated, the execution of the fallback.

* * * * *